United States Patent [19]

Wilson et al.

[11] Patent Number: 5,677,151
[45] Date of Patent: Oct. 14, 1997

[54] THERMOSTABLE CELLULASE FROM A THERMOMONOSPORA GENE

[75] Inventors: David B. Wilson; Larry P. Walker; Sheng Zhang, all of Ithaca, N.Y.

[73] Assignee: Cornell Research Foundation, Inc., Ithaca, N.Y.

[21] Appl. No.: 265,429

[22] Filed: Jun. 24, 1994

[51] Int. Cl.$^6$ .............................. C12P 19/20; C12N 9/26; A61K 38/47; C07H 21/04
[52] U.S. Cl. .............................. 435/72; 435/96; 435/201; 435/252.3; 435/320.1; 424/94.61; 536/23.7
[58] Field of Search ........................... 435/96, 72, 252.3, 435/320.1, 201; 536/23.7; 424/94.61

[56] References Cited

U.S. PATENT DOCUMENTS

| | | | |
|---|---|---|---|
| 5,232,851 | 8/1993 | Cox et al. | 435/263 |
| 5,318,905 | 6/1994 | Saito et al. | 435/209 |

OTHER PUBLICATIONS

Bothwell, M.K. et al. (1993) "Synergism between pure Thermomonospora fusca and Trichoderma reesei cellulases" Biomass and Bioenergy. 4(4):293–299 1993.

Irwin et al., "Activity Studies of Eight Purified Cellulases: Specificity, Synergism, and Binding Domain Effects", *Biotechnology and Bioengineering*, vol. 42, 1993, pp. 1002–1013.

Walker et al., "Engineering Cellulase Mixtures by Varying the Mole Fraction of Thermomonospora fusca E$_5$ and E$_3$, Trichoderma reesei CBHI, and Caldocellum saccharolyticum, β–Glucosidase *Biotechnology and Bioengineering*", vol. 42, 1993, pp. 1019–1028.

Wilson, D.B. (1992) "Biochemistry and genetics of actinomycete cellulases" *Critical Rev. in Biotechnol.* 12(1/2):45–63.

Woodward, J. et al. (1988) "Hydrolysis of cellulose by saturating and non–saturating concentrations of cellulase: implications for synergism" Bio/technology. 6:301–304. Mar. 1988.

Walker, L.P. et al. (1992) "Fragmentation of cellulose by the major Thermomonospora fusca cellulases, Trichoderma reesei CBHI, and their mixtures", Biotech. and Bioeng. 40:1019–1026. 1992.

Lao, G. and Wilson, D.B. (1992) "Cloning and sequencing of exocellulase and a protease from *T. fusca*," *Abstr. Gen. Meet. Am. Soc. Microbiol.* 92(0):314.

*Primary Examiner*—Robert A. Wax
*Assistant Examiner*—Kawai Lau
*Attorney, Agent, or Firm*—Hodgson, Russ, Andrews, Woods & Goodyear

[57] ABSTRACT

The invention relates to a gene isolated from *Thermomonospora fusca*, wherein the gene encodes a thermostable cellulase. Disclosed is the nucleotide sequence of the *T. fusca* gene; and nucleic acid molecules comprising the gene, or a fragment of the gene, that can be used to recombinantly express the cellulase or a catalytically active polypeptide thereof, respectively. The isolated and purified recombinant cellulase or catalytically active polypeptide may be used to hydrolyze substrate either by itself; or in combination with other cellulases, with the resultant combination having unexpected hydrolytic activity.

16 Claims, 1 Drawing Sheet

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 3404 nucleotides
        ( B ) TYPE: nucleic acid
        ( C ) STRANDEDNESS: double- stranded
        ( D ) TOPOLOGY: linear ( i i ) MOLECULE TYPE: Genomic DNA ( i i i ) ORIGINAL SOURCE:
 ( A ) ORGANISM: Thermomonospora fusca
 ( B ) STRAIN: YX36
 ( C ) CELL TYPE: bacterium ( i v ) SEQUENCE DESCRIPTION: SEQ ID NO:1:

| | | | | | |
|---|---|---|---|---|---|
| TGTTCCGTTC | CGTCACCATC | CTTGCGCGTC | CCGGCGGAGG | GGGGAAGCAC | 50 |
| CCCGCGAGAT | GGCTCCGCCA | CGGCCTGTTT | CCGACCCCCG | TCACAAAAGC | 100 |
| CCATTTAACG | CGGTATTTAC | AACCGGTCAT | GAAGTGGCTA | CTCTCTTTTG | 150 |
| GGAGCGCTCC | CGTGCCGCTA | GTCACACTGG | GACGTGAATG | GCGTCACGGT | 200 |
| AGGGCTCGTC | GTGTGACACG | CATTTCGAC | CCTGCTTTAA | GTCCCTAAGT | 250 |
| GGGAGCGCTC | CCAGCCTTCG | GGAGAACTCC | CACACAACCA | ACCGTCCGAC | 300 |
| GCCACTCTCC | CAGCGCTCAA | ACGGAGGCAG | CAGTGTTCAC | CATCCCCCGC | 350 |
| TCCCCTCCGG | GGCGCCCGGC | CGTCGTCCGC | GCAACCACGC | CGACCGGTCG | 400 |
| GCTGAACACT | GCAGCGTCCG | GTTCTCGACC | ATCCCCTTGC | GAGAGAACAT | 450 |
| CCTCCAACCA | AGGAAGACAC | CGAT ATG AGT AAA GTT CGT GCC ACG | | | 495 |
| | | Met Ser Lys Val Arg Ala Thr | | | |
| | | 1 5 | | | |

| AAC | AGA | CGT | TCG | TGG | ATG | CGG | CGC | GGC | CTG | GCA | GCC | GCC | TCT | 537 |
|---|---|---|---|---|---|---|---|---|---|---|---|---|---|---|
| Asn | Arg | Arg | Ser | Trp | Met | Arg | Arg | Gly | Leu | Ala | Ala | Ala | Ser | |
| | | 10 | | | | 15 | | | | | 20 | | | |

| GGA | CTG | GCG | CTT | GGC | GCC | TCC | ATG | GTG | GCG | TTC | GCT | GCT | CCG | 579 |
|---|---|---|---|---|---|---|---|---|---|---|---|---|---|---|
| Gly | Leu | Ala | Leu | Gly | Ala | Ser | Met | Val | Ala | Phe | Ala | Ala | Pro | |
| | | | 25 | | | | | 30 | | | | | 35 | |

| GCC | AAC | GCC | GCC | GGC | TGC | TCG | GTG | GAC | TAC | ACG | GTC | AAC | TCC | 621 |
|---|---|---|---|---|---|---|---|---|---|---|---|---|---|---|
| Ala | Asn | Ala | Ala | Gly | Cys | Ser | Val | Asp | Tyr | Thr | Val | Asn | Ser | |
| | | | | 40 | | | | | 45 | | | | | |

| TGG | GGT | ACC | GGG | TTC | ACC | GCC | AAC | GTC | ACC | ATC | ACC | AAC | CTC | 663 |
|---|---|---|---|---|---|---|---|---|---|---|---|---|---|---|
| Trp | Gly | Thr | Gly | Phe | Thr | Ala | Asn | Val | Thr | Ile | Thr | Asn | Leu | |
| 50 | | | | 55 | | | | | 60 | | | | | |

| GGC | AGT | GCG | ATC | AAC | GGC | TGG | ACC | CTG | GAG | TGG | GAC | TTC | CCC | 705 |
|---|---|---|---|---|---|---|---|---|---|---|---|---|---|---|
| Gly | Ser | Ala | Ile | Asn | Gly | Trp | Thr | Leu | Glu | Trp | Asp | Phe | Pro | |
| | 65 | | | | 70 | | | | | 75 | | | | |

| GGC | AAC | CAG | CAG | GTG | ACC | AAC | CTG | TGG | AAC | GGG | ACC | TAC | ACC | 747 |
|---|---|---|---|---|---|---|---|---|---|---|---|---|---|---|
| Gly | Asn | Gln | Gln | Val | Thr | Asn | Leu | Trp | Asn | Gly | Thr | Tyr | Thr | |
| | | 80 | | | | | 85 | | | | | 90 | | |

| CAG | TCC | GGG | CAG | CAC | GTG | TCG | GTC | AGC | AAC | GCC | CCG | TAC | AAC | 789 |
|---|---|---|---|---|---|---|---|---|---|---|---|---|---|---|
| Gln | Ser | Gly | Gln | His | Val | Ser | Val | Ser | Asn | Ala | Pro | Tyr | Asn | |
| | | | 95 | | | | | 100 | | | | | 105 | |

| GCC | TCC | ATC | CCG | GCC | AAC | GGA | ACG | GTT | GAG | TTC | GGG | TTC | AAC | 831 |
|---|---|---|---|---|---|---|---|---|---|---|---|---|---|---|
| Ala | Ser | Ile | Pro | Ala | Asn | Gly | Thr | Val | Glu | Phe | Gly | Phe | Asn | |
| | | | | 110 | | | | | 115 | | | | | |

| GGC | TCC | TAC | TCG | GGC | AGC | AAC | GAC | ATC | CCC | TCC | TCC | TTC | AAG | 873 |
|---|---|---|---|---|---|---|---|---|---|---|---|---|---|---|
| Gly | Ser | Tyr | Ser | Gly | Ser | Asn | Asp | Ile | Pro | Ser | Ser | Phe | Lys | |
| 120 | | | | | 125 | | | | | 130 | | | | |

| CTG | AAC | GGG | GTT | ACC | TGC | GAC | GGC | TCG | GAC | GAC | CCC | GAC | CCC | 915 |
|---|---|---|---|---|---|---|---|---|---|---|---|---|---|---|
| Leu | Asn | Gly | Val | Thr | Cys | Asp | Gly | Ser | Asp | Asp | Pro | Asp | Pro | |
| | 135 | | | | | 140 | | | | | 145 | | | |

| GAG | CCC | AGC | CCC | TCC | CCC | AGC | CCT | TCC | CCC | AGC | CCC | ACA | GAC | 957 |
|---|---|---|---|---|---|---|---|---|---|---|---|---|---|---|
| Glu | Pro | Ser | Pro | Ser | Pro | Ser | Pro | Ser | Pro | Ser | Pro | Thr | Asp | |
| | | 150 | | | | | 155 | | | | | 160 | | |

| CCG | GAT | GAG | CCG | GGC | GGC | CCG | ACC | AAC | CCG | CCC | ACC | AAC | CCC | 999 |
|---|---|---|---|---|---|---|---|---|---|---|---|---|---|---|
| Pro | Asp | Glu | Pro | Gly | Gly | Pro | Thr | Asn | Pro | Pro | Thr | Asn | Pro | |
| | | | 165 | | | | | 170 | | | | | 175 | |

| GGC | GAG | AAG | GTC | GAC | AAC | CCG | TTC | GAG | GGC | GCC | AAG | CTG | TAC | 1041 |
|---|---|---|---|---|---|---|---|---|---|---|---|---|---|---|

| | | | | | | | | | | | | | |
|---|---|---|---|---|---|---|---|---|---|---|---|---|---|
| Gly | Glu | Lys | Val | Asp | Asn | Pro | Phe | Glu | Gly | Ala | Lys | Leu | Tyr |
| | | | 180 | | | | | 185 | | | | | |

| | | | | | | | | | | | | | |
|---|---|---|---|---|---|---|---|---|---|---|---|---|---|
| GTG | AAC | CCG | GTC | TGG | TCG | GCC | AAG | GCC | GCC | GCT | GAG | CCG | GGC | 1083
| Val | Asn | Pro | Val | Trp | Ser | Ala | Lys | Ala | Ala | Ala | Glu | Pro | Gly |
| 190 | | | | | 195 | | | | | 200 | | | |

| GGT | TCC | GCG | GTC | GCC | AAC | GAG | TCC | ACC | GCT | GTC | TGG | CTG | GAC | 1125 |
|---|---|---|---|---|---|---|---|---|---|---|---|---|---|---|
| Gly | Ser | Ala | Val | Ala | Asn | Glu | Ser | Thr | Ala | Val | Trp | Leu | Asp | |
| | 205 | | | | | 210 | | | | | 215 | | | |

| CGT | ATC | GGC | GCC | ATC | GAG | GGC | AAC | GAC | AGC | CCG | ACC | ACC | GGC | 1167 |
|---|---|---|---|---|---|---|---|---|---|---|---|---|---|---|
| Arg | Ile | Gly | Ala | Ile | Glu | Gly | Asn | Asp | Ser | Pro | Thr | Thr | Gly | |
| | | 220 | | | | | 225 | | | | | 230 | | |

| TCC | ATG | GGT | CTG | CGC | GAC | CAC | CTG | GAG | GAG | GCC | GTC | CGC | CAG | 1209 |
|---|---|---|---|---|---|---|---|---|---|---|---|---|---|---|
| Ser | Met | Gly | Leu | Arg | Asp | His | Leu | Glu | Glu | Ala | Val | Arg | Gln | |
| | | | 235 | | | | | 240 | | | | | 245 | |

| TCC | GGT | GGC | GAC | CCG | CTG | ACC | ATC | CAG | GTC | GTC | ATC | TAC | AAC | 1251 |
|---|---|---|---|---|---|---|---|---|---|---|---|---|---|---|
| Ser | Gly | Gly | Asp | Pro | Leu | Thr | Ile | Gln | Val | Val | Ile | Tyr | Asn | |
| | | | | 250 | | | | | 255 | | | | | |

| CTG | CCC | GGC | CGC | GAC | TGC | GCC | GCG | CTG | GCC | TCC | AAC | GGT | GAG | 1293 |
|---|---|---|---|---|---|---|---|---|---|---|---|---|---|---|
| Leu | Pro | Gly | Arg | Asp | Cys | Ala | Ala | Leu | Ala | Ser | Asn | Gly | Glu | |
| 260 | | | | | 265 | | | | | 270 | | | | |

| CTG | GGT | CCC | GAT | GAA | CTC | GAC | CGC | TAC | AAG | AGC | GAG | TAC | ATC | 1335 |
|---|---|---|---|---|---|---|---|---|---|---|---|---|---|---|
| Leu | Gly | Pro | Asp | Glu | Leu | Asp | Arg | Tyr | Lys | Ser | Glu | Tyr | Ile | |
| | 275 | | | | | 280 | | | | | 285 | | | |

| GAC | CCG | ATC | GCC | GAC | ATC | ATG | TGG | GAC | TTC | GCA | GAC | TAC | GAG | 1377 |
|---|---|---|---|---|---|---|---|---|---|---|---|---|---|---|
| Asp | Pro | Ile | Ala | Asp | Ile | Met | Trp | Asp | Phe | Ala | Asp | Tyr | Glu | |
| | | 290 | | | | | 295 | | | | | 300 | | |

| AAC | CTG | CGG | ATC | GTC | GCC | ATC | ATC | GAG | ATC | GAC | TCC | CTG | CCC | 1419 |
|---|---|---|---|---|---|---|---|---|---|---|---|---|---|---|
| Asn | Leu | Arg | Ile | Val | Ala | Ile | Ile | Glu | Ile | Asp | Ser | Leu | Pro | |
| | | | 305 | | | | | 310 | | | | | 315 | |

| AAC | CTC | GTC | ACC | AAC | GTG | GGC | GGG | AAC | GGC | GGC | ACC | GAG | CTC | 1461 |
|---|---|---|---|---|---|---|---|---|---|---|---|---|---|---|
| Asn | Leu | Val | Thr | Asn | Val | Gly | Gly | Asn | Gly | Gly | Thr | Glu | Leu | |
| | | | | 320 | | | | | 325 | | | | | |

| TGC | GCC | TAC | ATG | AAG | CAG | AAC | GGC | GGC | TAC | GTC | AAC | GGT | GTC | 1503 |
|---|---|---|---|---|---|---|---|---|---|---|---|---|---|---|
| Cys | Ala | Tyr | Met | Lys | Gln | Asn | Gly | Gly | Tyr | Val | Asn | Gly | Val | |
| 330 | | | | | 335 | | | | | 340 | | | | |

| GGC | TAC | GCC | CTC | CGC | AAG | CTG | GGC | GAG | ATC | CCG | AAC | GTC | TAC | 1545 |
|---|---|---|---|---|---|---|---|---|---|---|---|---|---|---|
| Gly | Tyr | Ala | Leu | Arg | Lys | Leu | Gly | Glu | Ile | Pro | Asn | Val | Tyr | |
| | 345 | | | | | 350 | | | | | 355 | | | |

| AAC | TAC | ATC | GAC | GCC | GCC | CAC | CAC | GGC | TGG | ATC | GGC | TGG | GAC | 1587 |
|---|---|---|---|---|---|---|---|---|---|---|---|---|---|---|
| Asn | Tyr | Ile | Asp | Ala | Ala | His | His | Gly | Trp | Ile | Gly | Trp | Asp | |
| | | 360 | | | | | 365 | | | | | 370 | | |

| TCC | AAC | TTC | GGC | CCC | TCG | GTG | GAC | ATC | TTC | TAC | GAG | GCC | GCC | 1629 |
|---|---|---|---|---|---|---|---|---|---|---|---|---|---|---|
| Ser | Asn | Phe | Gly | Pro | Ser | Val | Asp | Ile | Phe | Tyr | Glu | Ala | Ala | |
| | | | 375 | | | | | 380 | | | | | 385 | |

| AAC | GCC | TCC | GGC | TCC | ACC | GTG | GAC | TAC | GTG | CAC | GGC | TTC | ATC | 1671 |
|---|---|---|---|---|---|---|---|---|---|---|---|---|---|---|
| Asn | Ala | Ser | Gly | Ser | Thr | Val | Asp | Tyr | Val | His | Gly | Phe | Ile | |
| | | | | 390 | | | | | 395 | | | | | |

| TCC | AAC | ACG | GCC | AAC | TAC | TCG | GCC | ACT | GTG | GAG | CCG | TAC | CTG | 1713 |
|---|---|---|---|---|---|---|---|---|---|---|---|---|---|---|
| Ser | Asn | Thr | Ala | Asn | Tyr | Ser | Ala | Thr | Val | Glu | Pro | Tyr | Leu | |
| 400 | | | | | 405 | | | | | 410 | | | | |

| GAC | GTC | AAC | GGC | ACC | GTT | AAC | GGC | CAG | CTC | ATC | CGC | CAG | TCC | 1755 |
|---|---|---|---|---|---|---|---|---|---|---|---|---|---|---|
| Asp | Val | Asn | Gly | Thr | Val | Asn | Gly | Gln | Leu | Ile | Arg | Gln | Ser | |
| | 415 | | | | | 420 | | | | | 425 | | | |

| AAG | TGG | GTT | GAC | TGG | AAC | CAG | TAC | GTC | GAC | GAG | CTC | TCC | TTC | 1797 |
|---|---|---|---|---|---|---|---|---|---|---|---|---|---|---|
| Lys | Trp | Val | Asp | Trp | Asn | Gln | Tyr | Val | Asp | Glu | Leu | Ser | Phe | |
| | | 430 | | | | | 435 | | | | | 440 | | |

| GTC | CAG | GAC | CTG | CGT | CAG | GCC | CTG | ATC | GCC | AAG | GGC | TTC | CGG | 1839 |
|---|---|---|---|---|---|---|---|---|---|---|---|---|---|---|
| Val | Gln | Asp | Leu | Arg | Gln | Ala | Leu | Ile | Ala | Lys | Gly | Phe | Arg | |
| | | | 445 | | | | | 450 | | | | | 455 | |

| TCC | GAC | ATC | GGT | ATG | CTC | ATC | GAC | ACC | TCC | CGC | AAC | GGC | TGG | 1881 |
|---|---|---|---|---|---|---|---|---|---|---|---|---|---|---|

| Ser | Asp | Ile | Gly | Met | Leu | Ile | Asp | Thr | Ser | Arg | Asn | Gly | Trp | |
|-----|-----|-----|-----|-----|-----|-----|-----|-----|-----|-----|-----|-----|-----|--|
| | | | | 460 | | | | | 465 | | | | | |

| GGT | GGC | CCG | AAC | CGT | CCG | ACC | GGA | CCG | AGC | TCC | TCC | ACC | GAC | 1923 |
|-----|-----|-----|-----|-----|-----|-----|-----|-----|-----|-----|-----|-----|-----|------|
| Gly | Gly | Pro | Asn | Arg | Pro | Thr | Gly | Pro | Ser | Ser | Ser | Thr | Asp | |
| 470 | | | | | 475 | | | | | 480 | | | | |

| CTC | AAC | ACC | TAC | GTT | GAC | GAG | AGC | CGT | ATC | GAC | CGC | CGT | ATC | 1965 |
|-----|-----|-----|-----|-----|-----|-----|-----|-----|-----|-----|-----|-----|-----|------|
| Leu | Asn | Thr | Tyr | Val | Asp | Glu | Ser | Arg | Ile | Asp | Arg | Arg | Ile | |
| | 485 | | | | | 490 | | | | | 495 | | | |

| CAC | CCC | GGT | AAC | TGG | TGC | AAC | CAG | GCC | GGT | GCG | GGC | CTC | GGC | 2007 |
|-----|-----|-----|-----|-----|-----|-----|-----|-----|-----|-----|-----|-----|-----|------|
| His | Pro | Gly | Asn | Trp | Cys | Asn | Gln | Ala | Gly | Ala | Gly | Leu | Gly | |
| | | 500 | | | | | 505 | | | | | 510 | | |

| GAG | CGG | CCC | ACG | GTC | AAC | CCG | GCT | CCC | GGT | GTT | GAC | GCC | TAC | 2049 |
|-----|-----|-----|-----|-----|-----|-----|-----|-----|-----|-----|-----|-----|-----|------|
| Glu | Arg | Pro | Thr | Val | Asn | Pro | Ala | Pro | Gly | Val | Asp | Ala | Tyr | |
| | | | 515 | | | | | 520 | | | | | 525 | |

| GTC | TGG | GTG | AAG | CCC | CCG | GGT | GAG | TCC | GAC | GGC | GCC | AGC | GAG | 2091 |
|-----|-----|-----|-----|-----|-----|-----|-----|-----|-----|-----|-----|-----|-----|------|
| Val | Trp | Val | Lys | Pro | Pro | Gly | Glu | Ser | Asp | Gly | Ala | Ser | Glu | |
| | | | | 530 | | | | | 535 | | | | | |

| GAG | ATC | CCG | AAC | GAC | GAG | GGC | AAG | GGC | TTC | GAC | CGC | ATG | TGC | 2133 |
|-----|-----|-----|-----|-----|-----|-----|-----|-----|-----|-----|-----|-----|-----|------|
| Glu | Ile | Pro | Asn | Asp | Glu | Gly | Lys | Gly | Phe | Asp | Arg | Met | Cys | |
| 540 | | | | | 545 | | | | | 550 | | | | |

| GAC | CCG | ACC | TAC | CAG | GGC | AAC | GCC | CGC | AAC | GGC | AAC | AAC | CCC | 2175 |
|-----|-----|-----|-----|-----|-----|-----|-----|-----|-----|-----|-----|-----|-----|------|
| Asp | Pro | Thr | Tyr | Gln | Gly | Asn | Ala | Arg | Asn | Gly | Asn | Asn | Pro | |
| | 555 | | | | | 560 | | | | | 565 | | | |

| TCG | GGT | GCG | CTG | CCC | AAC | GCC | CCC | ATC | TCC | GGC | CAC | TGG | TTC | 2217 |
|-----|-----|-----|-----|-----|-----|-----|-----|-----|-----|-----|-----|-----|-----|------|
| Ser | Gly | Ala | Leu | Pro | Asn | Ala | Pro | Ile | Ser | Gly | His | Trp | Phe | |
| | | 570 | | | | | 575 | | | | | 580 | | |

| TCT | GCC | CAG | TTC | CGC | GAG | CTG | CTG | GCC | AAC | GCC | TAC | CCG | CCT | 2259 |
|-----|-----|-----|-----|-----|-----|-----|-----|-----|-----|-----|-----|-----|-----|------|
| Ser | Ala | Gln | Phe | Arg | Glu | Leu | Leu | Ala | Asn | Ala | Tyr | Pro | Pro | |
| | | | 585 | | | | | 590 | | | | | 595 | |

| CTG | TAAAGC | GGAGTGAGGC | AACGGCTGAC | AGCCTCAACG | AGGAACTGAT | 2308 |
|-----|--------|------------|------------|------------|------------|------|
| Leu | | | | | | |

596

| CAGCACCTCC | TAGCCGGAGA | CGGCGCCCGT | CCACTCCCCG | TGGGCGGGCG | 2358 |
|------------|------------|------------|------------|------------|------|
| CCGCTTTTAT | GCCGACCCGT | GCCCCAGCCG | CAAGGGGCAC | GGGTCGGCCT | 2408 |
| ATTCCGGCGA | TGTCGGTCAC | GTCGCCCTAG | CACCCGGAAA | CGCCGAGAAA | 2458 |
| GACTGCCCCG | AAACGGTCCT | CTCCCATCCC | TGCATTAGGT | TGGCGCAGTC | 2508 |
| CGCCTATGGC | TTCGTGGGCC | GGAACCCAAC | CCACCATCAA | CGAGAGGTAT | 2558 |
| CACCATGGCC | AGTGTGGTGA | AATTCAATGT | GCTGACGGTT | CCTCCCGGTG | 2608 |
| CCGGCGCCAC | CCCGGAGGAC | GTTTGCCAAG | CGCGCAGGCC | TCGTGGAGAA | 2658 |
| CCGGGCCGGG | TTTGAGGAGT | TCCAACTGCT | GGCGCCCGGC | GACGGGACGG | 2708 |
| ACAAGTACAT | CGTCTACACG | CGCTGGCGCT | CCGGAGAGGA | CTACCAGAAC | 2758 |
| TGGCTGAACA | GCGAGGCCTT | CCAGCGCGGA | CACGCCCAGG | CCTCTGAAGA | 2808 |
| CTCCCGCCGC | AGCAGCCAGG | GCGGCCCGGC | CGCGTCCGCG | AGTGAACTCT | 2858 |
| GGTCCTTCGA | AGTCGTCCAG | CACGTCCAGG | CCCAGGACTG | ATCCGGTGC | 2908 |
| GGCCCTCGGT | TCTTTACCGG | GGGCCGCCCA | CCCCCTTCAT | CCCTTTTCTT | 2958 |
| CTCCCCCGCA | CCCCTTTTGA | TCTGCAATGA | TGGAATTTGC | GATTCTTGAG | 3008 |
| AAGGCCGATC | GTGTCCATGA | CTGCGCAGAA | GGCAGGACGA | CCACGCGTAC | 3058 |
| CGGTCGACAT | CGAAGGAGTC | AACTGACAGT | GGGGACTATC | GCGGGCTGA | 3108 |
| TTGTCGCGCT | GTCAGGCGTG | GGGATGGTCT | CGGCCAACGT | GCTCCCGTGG | 3158 |
| GAACCGTCGG | ACCCGGCATC | CGTGGTCCCC | GCCACCTCGC | AGGGCAGCAG | 3208 |

-continued

```
TTCTCCCATG ACGCCGGAGC CCTCGCGTCC CCGGTACCCC CACTCGTGCG    3258

CTCCGTGGTC GAAGAGGTGC CCAGCGCAAG CGGAGAACTG CGGGTCGTCG    3308

AAGGTGACGG GGAGGTCGTC GGCGAAGGCA CGCTCCTGCG CTACCTGGTG    3358

GAGGTCGAAG AAGGGCTTCC CGGAGACCCC GCCGACTTCG CTGCAG       3404
```

( 2 ) INFORMATION FOR SEQ ID NO:2:

( i ) SEQUENCE CHARACTERISTICS:
        ( A ) LENGTH: 20 nucleotides
        ( B ) TYPE: nucleic acid
        ( C ) STRANDEDNESS: single- stranded
        ( D ) TOPOLOGY: linear ( i i ) MOLECULE TYPE: DNA ( i i i ) IMMEDIATE SOURCE: synthesized ( i v ) ORIGINAL SOURCE:
        ( A ) ORGANISM: Thermomonospora fusca
        ( B ) STRAIN: YX36
        ( C ) CELL TYPE: bacterium ( v ) SEQUENCE DESCRIPTION: SEQ ID NO:2:

```
TTCGTCTTGC CGCCGATGCA    20
```

( 2 ) INFORMATION FOR SEQ ID NO:3:

( i ) SEQUENCE CHARACTERISTICS:
        ( A ) LENGTH: 40 nucleotides
        ( B ) TYPE: nucleic acid
        ( C ) STRANDEDNESS: single- stranded
        ( D ) TOPOLOGY: linear ( i i ) MOLECULE TYPE: DNA ( i i i ) IMMEDIATE SOURCE: synthesized ( i v ) ORIGINAL SOURCE:
        ( A ) ORGANISM: Thermomonospora fusca
        ( B ) STRAIN: YX36
        ( C ) CELL TYPE: bacterium ( v ) SEQUENCE DESCRIPTION: SEQ ID NO:3:

```
GCATCCACGA ACGTCTGTTC GTGGCACGAA CTTTACTCAT    40
```

( 2 ) INFORMATION FOR SEQ ID NO:4:

( i ) SEQUENCE CHARACTERISTICS:
        ( A ) LENGTH: 1269 nucleotides
        ( B ) TYPE: nucleic acid
        ( C ) STRANDEDNESS: double- stranded
        ( D ) TOPOLOGY: linear ( i i ) MOLECULE TYPE: genomic DNA ( i i i ) ORIGINAL SOURCE:
        ( A ) ORGANISM: Thermomonospora fusca
        ( B ) STRAIN: YX36
        ( C ) CELL TYPE: bacterium ( i v ) SEQUENCE DESCRIPTION: SEQ ID NO:4:

```
AAC  CCC  GGC  GAG  AAG  GTC  GAC  AAC  CCG  TTC  GAG  GGC  GCC  AAG      42
Asn  Pro  Gly  Glu  Lys  Val  Asp  Asn  Pro  Phe  Glu  Gly  Ala  Lys
 1             5                        10

CTG  TAC  GTG  AAC  CCG  GTC  TGG  TCG  GCC  AAG  GCC  GCC  GCT  GAG      84
Leu  Tyr  Val  Asn  Pro  Val  Trp  Ser  Ala  Lys  Ala  Ala  Ala  Glu
15                  20                      25

CCG  GGC  GGT  TCC  GCG  GTC  GCC  AAC  GAG  TCC  ACC  GCT  GTC  TGG     126
Pro  Gly  Gly  Ser  Ala  Val  Ala  Asn  Glu  Ser  Thr  Ala  Val  Trp
```

|  |  |  |  |  |  |  |  |  |  |  |
|---|---|---|---|---|---|---|---|---|---|---|
| | 30 | | | | 35 | | | | 40 | |
| CTG | GAC | CGT | ATC | GGC | GCC | ATC | GAG | GGC | AAC | GAC AGC CCG ACC | 168 |
| Leu | Asp | Arg | Ile | Gly | Ala | Ile | Glu | Gly | Asn | Asp Ser Pro Thr |
| | | 45 | | | | 50 | | | | 55 |
| ACC | GGC | TCC | ATG | GGT | CTG | CGC | GAC | CAC | CTG | GAG GAG GCC GTC | 210 |
| Thr | Gly | Ser | Met | Gly | Leu | Arg | Asp | His | Leu | Glu Glu Ala Val |
| | | | 60 | | | | 65 | | | 70 |
| CGC | CAG | TCC | GGT | GGC | GAC | CCG | CTG | ACC | ATC | CAG GTC GTC ATC | 252 |
| Arg | Gln | Ser | Gly | Gly | Asp | Pro | Leu | Thr | Ile | Gln Val Val Ile |
| | | | | 75 | | | | 80 |
| TAC | AAC | CTG | CCC | GGC | CGC | GAC | TGC | GCC | GCG | CTG GCC TCC AAC | 294 |
| Tyr | Asn | Leu | Pro | Gly | Arg | Asp | Cys | Ala | Ala | Leu Ala Ser Asn |
| 85 | | | | | 90 | | | | | 95 |
| GGT | GAG | CTG | GGT | CCC | GAT | GAA | CTC | GAC | CGC | TAC AAG AGC GAG | 336 |
| Gly | Glu | Leu | Gly | Pro | Asp | Glu | Leu | Asp | Arg | Tyr Lys Ser Glu |
| | 100 | | | | | 105 | | | | 110 |
| TAC | ATC | GAC | CCG | ATC | GCC | GAC | ATC | ATG | TGG | GAC TTC GCA GAC | 378 |
| Tyr | Ile | Asp | Pro | Ile | Ala | Asp | Ile | Met | Trp | Asp Phe Ala Asp |
| | | | 115 | | | | 120 | | | 125 |
| TAC | GAG | AAC | CTG | CGG | ATC | GTC | GCC | ATC | ATC | GAG ATC GAC TCC | 420 |
| Tyr | Glu | Asn | Leu | Arg | Ile | Val | Ala | Ile | Ile | Glu Ile Asp Ser |
| | | | | 130 | | | | 135 | | | 140 |
| CTG | CCC | AAC | CTC | GTC | ACC | AAC | GTG | GGC | GGG | AAC GGC GGC ACC | 462 |
| Leu | Pro | Asn | Leu | Val | Thr | Asn | Val | Gly | Gly | Asn Gly Gly Thr |
| | | | | 145 | | | | 150 |
| GAG | CTC | TGC | GCC | TAC | ATG | AAG | CAG | AAC | GGC | GGC TAC GTC AAC | 504 |
| Glu | Leu | Cys | Ala | Tyr | Met | Lys | Gln | Asn | Gly | Gly Tyr Val Asn |
| 155 | | | | | 160 | | | | | 165 |
| GGT | GTC | GGC | TAC | GCC | CTC | CGC | AAG | CTG | GGC | GAG ATC CCG AAC | 546 |
| Gly | Val | Gly | Tyr | Ala | Leu | Arg | Lys | Leu | Gly | Glu Ile Pro Asn |
| | 170 | | | | | 175 | | | | 180 |
| GTC | TAC | AAC | TAC | ATC | GAC | GCC | GCC | CAC | CAC | GGC TGG ATC GGC | 588 |
| Val | Tyr | Asn | Tyr | Ile | Asp | Ala | Ala | His | His | Gly Trp Ile Gly |
| | | | 185 | | | | 190 | | | 195 |
| TGG | GAC | TCC | AAC | TTC | GGC | CCC | TCG | GTG | GAC | ATC TTC TAC GAG | 630 |
| Trp | Asp | Ser | Asn | Phe | Gly | Pro | Ser | Val | Asp | Ile Phe Tyr Glu |
| | | | | 200 | | | | 205 | | | 210 |
| GCC | GCC | AAC | GCC | TCC | GGC | TCC | ACC | GTG | GAC | TAC GTG CAC GGC | 672 |
| Ala | Ala | Asn | Ala | Ser | Gly | Ser | Thr | Val | Asp | Tyr Val His Gly |
| | | | | 215 | | | | 220 |
| TTC | ATC | TCC | AAC | ACG | GCC | AAC | TAC | TCG | GCC | ACT GTG GAG CCG | 714 |
| Phe | Ile | Ser | Asn | Thr | Ala | Asn | Tyr | Ser | Ala | Thr Val Glu Pro |
| 225 | | | | | 230 | | | | | 235 |
| TAC | CTG | GAC | GTC | AAC | GGC | ACC | GTT | AAC | GGC | CAG CTC ATC CGC | 756 |
| Tyr | Leu | Asp | Val | Asn | Gly | Thr | Val | Asn | Gly | Gln Leu Ile Arg |
| | 240 | | | | | 245 | | | | 250 |
| CAG | TCC | AAG | TGG | GTT | GAC | TGG | AAC | CAG | TAC | GTC GAC GAG CTC | 798 |
| Gln | Ser | Lys | Trp | Val | Asp | Trp | Asn | Gln | Tyr | Val Asp Glu Leu |
| | | 255 | | | | 260 | | | | 265 |
| TCC | TTC | GTC | CAG | GAC | CTG | CGT | CAG | GCC | CTG | ATC GCC AAG GGC | 840 |
| Ser | Phe | Val | Gln | Asp | Leu | Arg | Gln | Ala | Leu | Ile Ala Lys Gly |
| | | | 270 | | | | 275 | | | 280 |
| TTC | CGG | TCC | GAC | ATC | GGT | ATG | CTC | ATC | GAC | ACC TCC CGC AAC | 882 |
| Phe | Arg | Ser | Asp | Ile | Gly | Met | Leu | Ile | Asp | Thr Ser Arg Asn |
| | | | | 285 | | | | 290 |
| GGC | TGG | GGT | GGC | CCG | AAC | CGT | CCG | ACC | GGA | CCG AGC TCC TCC | 924 |
| Gly | Trp | Gly | Gly | Pro | Asn | Arg | Pro | Thr | Gly | Pro Ser Ser Ser |
| 295 | | | | | 300 | | | | | 305 |
| ACC | GAC | CTC | AAC | ACC | TAC | GTT | GAC | GAG | AGC | CGT ATC GAC CGC | 966 |
| Thr | Asp | Leu | Asn | Thr | Tyr | Val | Asp | Glu | Ser | Arg Ile Asp Arg |

|  |  |  |  |  |  |  |  |  |  |  |  |  |  |
|---|---|---|---|---|---|---|---|---|---|---|---|---|---|
|  |  | 310 |  |  |  | 315 |  |  |  |  | 320 |  |  |
| CGT | ATC | CAC | CCC | GGT | AAC | TGG | TGC | AAC | CAG | GCC | GGT | GCG | GGC | 1008 |
| Arg | Ile | His | Pro | Gly | Asn | Trp | Cys | Asn | Gln | Ala | Gly | Ala | Gly |
|  |  | 325 |  |  |  | 330 |  |  |  |  | 335 |  |
| CTC | GGC | GAG | CGG | CCC | ACG | GTC | AAC | CCG | GCT | CCC | GGT | GTT | GAC | 1050 |
| Leu | Gly | Glu | Arg | Pro | Thr | Val | Asn | Pro | Ala | Pro | Gly | Val | Asp |
|  |  |  | 340 |  |  |  |  | 345 |  |  |  |  | 350 |
| GCC | TAC | GTC | TGG | GTG | AAG | CCC | CCG | GGT | GAG | TCC | GAC | GGC | GCC | 1092 |
| Ala | Tyr | Val | Trp | Val | Lys | Pro | Pro | Gly | Glu | Ser | Asp | Gly | Ala |
|  |  |  |  | 355 |  |  |  |  | 360 |  |  |  |  |
| AGC | GAG | GAG | ATC | CCG | AAC | GAC | GAG | GGC | AAG | GGC | TTC | GAC | CGC | 1134 |
| Ser | Glu | Glu | Ile | Pro | Asn | Asp | Glu | Gly | Lys | Gly | Phe | Asp | Arg |
| 365 |  |  |  |  | 370 |  |  |  |  | 375 |  |  |  |
| ATG | TGC | GAC | CCG | ACC | TAC | CAG | GGC | AAC | GCC | CGC | AAC | GGC | AAC | 1176 |
| Met | Cys | Asp | Pro | Thr | Tyr | Gln | Gly | Asn | Ala | Arg | Asn | Gly | Asn |
|  | 380 |  |  |  |  | 385 |  |  |  |  | 390 |  |  |
| AAC | CCC | TCG | GGT | GCG | CTG | CCC | AAC | GCC | CCC | ATC | TCC | GGC | CAC | 1218 |
| Asn | Pro | Ser | Gly | Ala | Leu | Pro | Asn | Ala | Pro | Ile | Ser | Gly | His |
|  |  | 395 |  |  |  |  | 400 |  |  |  |  | 405 |  |
| TGG | TTC | TCT | GCC | CAG | TTC | CGC | GAG | CTG | CTG | GCC | AAC | GCC | TAC | 1260 |
| Trp | Phe | Ser | Ala | Gln | Phe | Arg | Glu | Leu | Leu | Ala | Asn | Ala | Tyr |
|  |  |  | 410 |  |  |  |  | 415 |  |  |  |  | 420 |
| CCG | CCT | CTG |  | 1269 |
| Pro | Pro | Leu |
|  |  | 423 |

( 2 ) INFORMATION FOR SEQ ID NO:5:

( i ) SEQUENCE CHARACTERISTICS:
        ( A ) LENGTH: 10 residues
        ( B ) TYPE: amino acid
        ( C ) TOPOLOGY: linear ( i i ) MOLECULE TYPE: protein ( i i i ) FRAGMENT TYPE: N-terminal ( i v ) ORIGINAL SOURCE:
        ( A ) ORGANISM: Escherichia coli
        ( B ) STRAIN: DH5'
        ( C ) CELL TYPE: bacterium
        ( D ) DEVELOPMENTAL STAGE: containing pSZ6

( v ) FEATURE: N-terminal sequence of recombinant E3

( v i ) SEQUENCE DESCRIPTION: SEQ ID NO:5:

| Ala | Gly | Cys | Ser | Val | Asp | Tyr | Thr | Val | Asn |
|---|---|---|---|---|---|---|---|---|---|
| 1 |  |  |  | 5 |  |  |  |  | 10 |

( 2 ) INFORMATION FOR SEQ ID NO:6:

( i ) SEQUENCE CHARACTERISTICS:
        ( A ) LENGTH: 10 residues
        ( B ) TYPE: amino acid
        ( C ) TOPOLOGY: linear ( i i ) MOLECULE TYPE: protein ( i i i ) FRAGMENT TYPE: N-terminal ( i v ) ORIGINAL SOURCE:
        ( A ) ORGANISM: Streptomyces lividans
        ( B ) STRAIN: TKM31
        ( C ) CELL TYPE: bacterium
        ( D ) DEVELOPMENTAL STAGE: containing pSZ7

( v ) FEATURE: N-terminal sequence of recombinant E3

( v i ) SEQUENCE DESCRIPTION: SEQ ID NO:6:

```
Ala Ala Pro Ala Gln Ala Ala Gly Cys Ser
 1           5                   10
```

( 2 ) INFORMATION FOR SEQ ID NO:7:

( i ) SEQUENCE CHARACTERISTICS:
        ( A ) LENGTH: 6 residues
        ( B ) TYPE: amino acid
        ( C ) TOPOLOGY: linear ( i i ) MOLECULE TYPE: protein ( i i i ) FRAGMENT TYPE: N-terminal ( i v ) ORIGINAL SOURCE:
        ( A ) ORGANISM: Streptomyces lividans
        ( B ) STRAIN: TKM31
        ( C ) CELL TYPE: bacterium
        ( D ) DEVELOPMENTAL STAGE: containing pSZ7

( v ) FEATURE: alternate N-terminal sequence of recombinant E3

( v i ) SEQUENCE DESCRIPTION: SEQ ID NO:7:

```
Ala Gly Cys Ser Val Asp
 1                    6
```

( 2 ) INFORMATION FOR SEQ ID NO:8:

( i ) SEQUENCE CHARACTERISTICS:
        ( A ) LENGTH: 10 residues
        ( B ) TYPE: amino acid
        ( C ) TOPOLOGY: linear ( i i ) MOLECULE TYPE: protein ( i i i ) FRAGMENT TYPE: N-terminal ( i v ) ORIGINAL SOURCE:
        ( A ) ORGANISM: Thermomonospora fusca
        ( B ) STRAIN: YX36
        ( C ) CELL TYPE: bacterium ( v ) FEATURE: N-terminal sequence of E3

( v i ) SEQUENCE DESCRIPTION: SEQ ID NO:8:

```
Ala Gly Cys Ser Val Asp Tyr Thr Val Asn
 1           5                       10
```

THERMOSTABLE CELLULASE FROM A THERMOMONOSPORA GENE

This invention was made with government support under grant number FG02-84ER13233 awarded by the United States Department of Energy. The government has certain rights in this invention.

FIELD OF THE INVENTION

The present invention relates to a gene encoding a cellulose-degrading enzyme. More particularly, the invention is directed to a *Thermomonospora fusca* gene encoding a cellulase that has several desirable properties including thermostability, activity in a wide pH range (5–11); and unexpected hydrolytic activity when combined in a mixture including other cellulases. The purified recombinant cellulase, individually or in combination with other enzymes, may be used in several industrial applications.

BACKGROUND OF THE INVENTION

Cellulases can be classified into two broad groups: endo-cellulases and exocellulases. A cellulase is an enzyme capable of hydrolyzing cellulose, a complex polyose that occurs in the microfibrils of plant cell walls. The products of the hydrolysis reaction include cellobiose or glucose, compounds that have a variety of applications as sources of fuel and chemicals. Thus, one application for a cellulase is to hydrolyze plant cellulose into its component glucose content, and then fermenting the resulting glucose into ethanol, in a method for producing fuel. For example, cellulase can be used in the process of converting the carbohydrates contained in agricultural cellulosic wastes, into ethanol.

Another application for cellulase is its usage in the paper and pulp industry. Cellulases have been used in the deinking and refining of recycled paper. In this application, utilizing a thermostable cellulase, i.e. having optimal activity at temperatures of 50° C. or higher versus having optimal activity at room temperature, could reduce the amount of enzyme used per ton of paper by as much as one fifth, and reduce the time of exposure to the enzyme needed to increase the brightness of the paper by one half. Reducing the concentration of enzyme and the time of exposure to the enzyme in the refining process, correspondingly and desirably reduces the reaction of the cellulase on the fibrils themselves and processing costs.

A cellulase having high thermostability has additional industrial applications where high temperatures are employed without having to increase the cellulase enzyme load to make up for the decreased enzyme activity occurring at high temperatures. The property of thermostability is especially important in food applications of cellulase, such as in the clarification of fruit juices. Cellulases have been used in combination with other enzymes to enhance yields while reducing the need for clarifying pectinase in extracting juice from fruits, or juice or soup flavorings from vegetables. Cellulases have also been used in combination with protease to dissociate dried seaweed which is then fermented with alcohol in the production of vinegar; and in combination with other enzymes as an alternative to potassium bromate dough conditioners in the baking industry.

Cellulases also have applications in the textile industry. The enzyme can be used to brighten and soften cotton fabrics by eating away microfibers on the surface that give clothes a dull look. More specifically, cellulases are being included as additives in formulating enzyme-containing detergents for soil removal, fabric softening, and color brightening. Thus, a thermostable cellulase that retains substantial enzyme activity at a wide range of temperatures would be particularly desirable as a detergent additive. Cellulases are also useful in textile processing. For example, U.S. Pat. No. 5,232,851 discloses the use of cellulase to treat nondyed and nonfinished cotton woven fabric resulting in improving characteristics of appearance and "feel" by removing fuzz and loose surface fibers. Cellulase is also utilized as a replacement to pumice in producing blue jeans having a "stone-washed" effect. Enzyme treatment appears to cause less damage to the jean fabric than lengthy exposure to pumice.

A thermostable cellulase that has significant activity at 60° C., in a pH range of 5.6–6.0, can be used to dissociate chitosan, a deacylated form of chitin, into a mixture of oligosaccha- rides. Deacylation of chitin into chitosan, with subsequent cellulase treatment of chitosan, can result in a renewable resource for the millions of tons of chitin-rich shells generated each year by seafood processors, rather than the current practice of disposing of the shells as garbage.

Therefore a need exists, in certain industrial applications, for a cellulase having enzyme activity and stability at tempera- tures greater than 40°–50° C., and in a pH range of 5–11. In general, higher hydrolysis reaction temperatures (greater than 50° C.) result in enhanced reaction kinetics (compared to reactions at less than 50° C.), provided that the cellulase is not rapidly denatured at the higher temperatures. Further, a combination of cellulases that result in unexpected hydrolytic activity (i.e., the hydrolytic activity of the mixture is greater than the sum of the hydrolytic activities of the individual cellulases comprising the mixture) would be desirable to reduce the amount of enzyme needed, and the time of exposure to the enzyme in an industrial process, thereby reducing process costs.

SUMMARY OF THE INVENTION

The present invention is directed to a *T. fusca* gene encoding a cellulase with the apparent molecular mass of the mature protein being about 65,000 daltons. Also, the invention is directed to a catalytically active polypeptide derived from the cellulase. A nucleic acid molecule containing the nucleic acid sequences of the present invention can be incorporated into vectors to form recombinant vectors, and the resultant recombinant vectors can then be introduced into a host cell system for the expression of the gene product ("E3"), or a catalytically active polypeptide thereof. The recombinant cellulase E3 exhibits significant enzyme activity at temperatures greater than 60° C. and at a pH range of from about 5–11. Unexpectedly, the recombinant E3 shows greater stability to proteolysis in culture supernatants as compared to other cellulases isolated from *T. fusca* (E2 and E5). Combining recombinant E3 with other cellulases results in a mixture having unexpected hydrolytic activity. Thus, the gene, the gene product, catalytically active polypeptide, and a combination of cellulases including the gene product, have novel properties useful in a variety of industrial applications.

BRIEF DESCRIPTION OF THE FIGURES

FIG. 1A shows the electrophoretic mobility of TE3 (lane 1), ErE3 (lane 2), and SrE3 (lane 3), on a 8.5% polyacrylamide gel stained with Coomassie blue.

FIG. 1B represents an electroblot of a 12% polyacrylamide gel onto a nitrocellulose membrane showing glycosylation analysis of ErE3 (lane 1), TE3 (lane 2) and SrE3 (lane 3) by labeling the protein with digoxigenin 3-0-succinyl-ε-aminocaproic acid hydrazide hydrochloride, and detection with anti-digoxigenin antibody coupled to alkaline phosphatase. Reference standards appear in lane 4.

DETAILED DESCRIPTION OF THE INVENTION

Figure 1A:
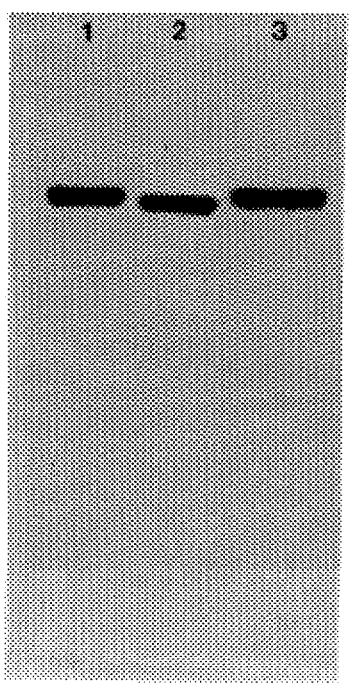
FIGS. 1A and 1B show electrophoretic mobilities of *T. fusca* E3 (TE3), and recombinantly produced E3 (*E. coli* E3, ErE3; and *S. lividans* E3, SE3) on an SDS-gel.

*Thermomonospora fusca* is a filamentous soil thermophile that produces cellulolytic, xylanolytic, and pectinolytic enzymes. Extracellular fluids from medium containing *T. fusca* cultures are crude enzyme preparations from which at least six bacterial cellulases, having a broad range of hydrolytic characteristics, may be purified. However, the number of cellulases each *T. fucsa* strain produces, may vary amongst strains (Wilson, D. B., 1988, Meth. Enzymol. 160:314–323; Walker et al., 1992, Biotechnol. Bioeng. 40:1019–1026). The present invention is directed to compositions comprising a cellulase of bacterial origin, wherein the purified recombinant enzyme has been designated E3.

In accordance with this invention, the nucleotide sequence of the gene encoding cellulase E3 is disclosed. The gene sequence described herein has been isolated from the thermophilic soil bacterium *T. fusca*. The nucleotide sequence of the present invention, SEQ ID NO:1, reveals that the amino acid sequence of the mature protein has a predicted molecular mass of about 59,646 daltons. According to one embodiment of the present invention, using recombinant DNA techniques, a nucleic acid molecule containing the gene encoding E3, or a gene fragment encoding the catalytic domain of E3, is incorporated into an expression vector, and the recombinant vector is introduced into an appropriate host cell thereby directing the expression of these sequences in that particular host cell. The expression system, comprising the recombinant vector introduced into the host cell, can be used to produce recombinant E3, or a recombinant catalytically active polypeptide, in the extracellular fluid from the culture. According to the present invention, recombinant E3 can be purified by methods known in the art including ion-exchange chromatography. Additionally, catalytically active polypeptides, i.e. containing cellulase activity, may be synthesized chemically from the amino acid sequence disclosed in the present invention, or may be produced from enzymatic or chemical cleavage of the purified mature recombinant protein E3. The thermostability of the enzyme compositions described herein, and activity at various pH ranges are disclosed.

The enzyme compositions of the invention, recombinant E3 or catalytically active polypeptide derived therefrom, can be used in an in vitro industrial process for a sufficient time to decrease the amount of the target substrate, such as cellulose or chitosan. The enzyme compositions are used by contacting the purified enzyme of the present invention with the substrate in the process at a temperature which will enhance the enzymatic activity of the enzyme. Temperatures at which the enzyme compositions of the present invention display enzymatic activity may range from approximately 30° C. to 70° C., wherein optimal or enhanced enzyme activity is observed at a range of approximately 50° C. to 70° C. A preferred range of temperatures for the enzymatic activity of the enzyme compositions of the present invention is 50° C. to 60° C. The preferred pH for enzymatic activity of the enzyme compositions of the present invention is a range of from pH 5-11. However, the pH within that range at which the enzyme composition is actually used necessarily depends on the particular process, and the inherent conditions at which the process must be, or desirably, is carried out. Further, the amount of time at which the substrate is exposed to, or treated with, the enzyme compositions of the present invention will vary depending on the amount of enzyme used, the amount of substrate contained in the process, the pH of the process, and the temperature at which the process is carried out.

Additionally, the present invention also comprises a particular combination of cellulases, which includes recombinant E3, wherein the mixture shows unexpected hydrolytic activity toward cellulose. Unexpected hydrolytic activity is used herein as meaning that the hydrolytic activity of the mixture containing the combination of cellulases according to the present invention, is greater than the sum of the hydrolytic activities of the individual cellulases comprising the mixture. Previously, it has been suggested that at least a trimixture of cellulases is necessary to effectively fragment and hydrolyze microcrystalline cellulose (Walker et al., 1992, supra). The present invention discloses a particular combination of cellulases which effectively fragments and hydrolyzes microcrystalline cellulose. The combination according to the present invention comprises a mixture of *T. fusca* cellulases E3 and E5, with *Trichoderma reesi* cellulase CBHI, wherein E3 is recombinant. Another embodiment of the present invention provides a combination of recombinant E3, E5, CBHI, and further includes β-glucosidase. In the method of using the combinations according to the present invention, it was found that a proper mole fraction of the cellulases is important for achieving the optimal unexpected hydrolytic activity.

In using the combination of cellulases according to the present invention, temperatures at which the combinations display enzymatic activity may range from approximately 30° C. to 70° C., wherein optimal enzyme activity is observed at a range of approximately 50° C. to 70° C. A preferred range of temperatures for the enzymatic activity of the enzyme combinations of the present invention are 50° C. to 60° C. The preferred pH for enzymatic activity of the combinations of the present invention is a range of from pH 4-6. However, the pH within that range at which the enzyme combination is actually used necessarily depends on the particular process, and its inherent conditions at which the process must be, or desirably, is carried out. Further, the amount of time at which the substrate is exposed to, or treated with, the enzyme combinations of the present invention will vary depending on the amount of the enzyme combination used, the amount of substrate contained in the process, the pH of the process, and the temperature at which the process is carried out.

For purposes of the description, the following embodiments illustrate the manner and process of making and using the invention and set forth the best mode contemplated by the inventor for carrying out the invention, but are not to be construed as limiting:

Embodiment A- Molecular cloning and sequencing of the *T. fusca* gene encoding E3;

Embodiment B- Characterization of the *T. fusca* gene encoding E3;

Embodiment C- Expression and purification of recombinant E3 and catalytically active polypeptide;

Embodiment D- Production of catalytically active polypeptide by cleavage of E3;

Embodiment E- Purification of recombinant E3 or catalytically active polypeptide;

Embodiment F- Physicochemical characterization of recombinant E3 and catalytically active polypeptide; and Embodiment G- Unexpected hydrolytic activity of the combination of recombinant E3, E5, and CBHI cellulases.

EMBODIMENT A

Molecular cloning and sequencing of the *T. fusca* gene encoding E3.

The strategy used to clone the gene encoding E3 was to purify E3 from *T. fusca* culture supernatant, chemically cleave the isolated protein into fragments, determine the N-terminal sequence of a fragment, and synthesize a probe which could be used to identify the gene encoding E3 in restricted *T. fusca* DNA by hybridization analysis.

E3 can be prepared from *T. fusca* cultures by first filtering the culture supernatant and obtaining a partially purified enzyme preparation by chromatographing the filtered culture supernatant on a phenyl SEPHAROSE™ column. The crude enzyme preparation is then loaded onto a p-nitrobenzyl 1-thio-β-D-cellobioside affinity column which had been equilibrated with 0.1M NaAc pH5 with 1 mM glucanolactone. A fraction containing E3 was then eluted by the addition of 0.1M lactose to the buffer used for equilibration. The fraction was then adjusted to pH4.5, diluted to 0.02M NaAc, and applied to an anion-exchange column. A linear NaCl gradient (0 to 0.5M) was used to elute fractions containing E3. E3 was further purified from the fractions resulting from anion exchange chromatography by adjusting the fractions to pH 6 in a buffer containing 1 mM $CaCl_2$, 1 mM $MgCl_2$, and 0.5 mM $MnCl_2$, and loading the fractions onto an affinity column containing Concanavalin A. Purified E3 was then eluted using the buffer containing 0.01M α-methylglucoside. The α-methylglucoside was removed from E3 by repeated dilution and concentration. The yield is about 35 mg of E3 from 350 mg of *T. fusca* crude.

E3 was chemically cleaved by dissolving E3 (3 mg) in 0.5 ml of 6M guanidine HCl/0.2M HCl, followed by the addition of 4 mg of cyanogen bromide. The mixture was incubated in the dark at room temperature for 24 hours, and then excess reagents and solvents were removed from the cleavage products by lyophilization and by washing on a concentrator. The cleavage products, E3 fragments, were separated by sodium dodecyl sulfate polyacrylamide amide gel electrophoresis (SDS-PAGE) and electrophoretically blotted onto membranes. A 12 kilodalton (kDa) band (E3p12) was cut out and its N-terminal sequence was determined using a protein sequenator. Corresponding to the complementary strand encoding the first 6 N-terminal amino acids of E3p12, degenerate oligonucleotides were synthesized (representative sequence disclosed in SEQ ID NO:2) and labelled by a 3' tailing reaction.

*T. fusca* chromosomal DNA was isolated and digested completely with Not I. Genomic Southern hybridization was carried out by electrophoresing the Not I-restricted *T. fusca* DNA on a 0.7% agarose gel, blotting the DNA fragments onto a nitrocellulose membrane, and hybridizing the E3p12 probe to the immobilized DNA fragments at 42° C. for 16 hours. The membrane was washed with 4XSSC plus 0.1% SDS once at room temperature and once at 47° C., and DNA fragments that hybridized to the probes were detected by an enzyme immunoassay using alkaline phosphatase. One positive band of approximately 7.1 kilobases (kb) was found on the membrane hybridized with the E3p12 probe. Therefore, a 7.1 kb fragment from the Not I digest of *T. fusca* DNA contained the gene encoding E3.

A genomic library was constructed by complete digestion of *T. fusca* DNA with Not I, electrophoresing the restriction fragments on an 0.8% low melting point agarose gel, cutting out gel slices containing DNA banding around 7.0 kb, purifying the DNA from the gel slices by β-agarase treatment, and then ligating the purified DNA to a plasmid (pBluescript SK+) that had been previously digested with Not I and dephosphorylated. DNA ligation mixtures were used to transform *Escherichia coli* DH5α, which then were plated on LB+Amp plates containing X-gal and IPTG to identify transformants. About 150 transformants were screened by hybridization of their DNA with the E3p12 probe. As a result of this screening procedure, four positive colonies were identified. The positive transformants were also tested by a carboxymethylcellulose (CMC) overlay assay at 50° C. for 24 hours as described by Teather et al. (1982, *Appl. Environ. Microbiol.* 43:777–780, herein incorporated by reference). These transformants were also tested by Western blotting preparations of the transformants with E3 antisera. All four transformants were positive by both assays. Plasmid DNA was prepared from all four transformants and restriction mapping showed that all of them contained a 7.1 kb Not I fragment. A plasmid, pSZ3, was identified as having the gene encoding E3 in the opposite orientation with respect to the plasmid lac promoter; while pSZ4 was identified as having the gene encoding E3 in the same orientation with respect to the lac promoter. It was noted that *E. coli* cells containing pSZ4, in which E3 gene is aligned with the lac promoter, showed more CMCase activity by the CMC overlay and expressed more E3 by Western blot analysis than cells with pSZ3 which have the gene encoding E3 in the opposite orientation.

To localize the E3 gene within the 7.1 kb fragment, pSZ3 was digested with Pst I and a 3.0 kb fragment was subcloned into the Pst I site of pUC18, and the ligation mixture was used to transform *E. coli* DH5α. The transformants were positive for the presence of E3 when tested by either the CMC overlay assay or by Western blotting preparations of the transformants with E3 antisera. Analysis of plasmid DNA, prepared from transformants, identified a plasmid, pSZ5, as having the gene encoding E3 in the opposite orientation with respect to the plasmid lac promoter; while pSZ6 was identified as having the gene encoding E3 in the same orientation with respect to the lac promoter. As consistent with expression from pSZ3 and pSZ4, *E. coli* cells containing pSZ6 showed more CMCase activity and expressed more E3 than cells containing pSZ5 which has the E3 gene in the opposite orientation with respect to the lac promoter.

Double-stranded DNA from pSZ6 and pSZ4 was used for sequencing the E3 structural gene and its 3' and 5' flanking regions. The sequences of both strands of the E3 gene were determine by the dideoxy-chain termination method. The universal primers for pUC/M13 sequencing, along with the E3p12 oligonucleotide, were used to determine the initial sequences within the inserts, and then specific primers for regions within the inserts were designed and synthesized. The use of both dGTP and DITP labelling mixtures and addition of ultrapure formamide (15–20% vol/vol) to the 6% polyacrylamide gels were performed to resolve band compressions resulting from the secondary structure because of the high G+C content of *T. fusca* DNA.

EMBODIMENT B

Characterization of the *T. fusca* E3 gene.

Sequence analysis software was used to determine the correct open reading frame, codon useage, base composition analysis, binding energies, deduced amino acid composition, and predicted molecular weight of the gene product. The cloned DNA had a G+C content of 66%, which agrees well with the 65% G+C content of *T. fusca* DNA reported previously (Lao et al., 1991, *J. Bacteriol.* 173:3397–3407) and the 67% G+C content of *T. curvata* DNA (Petricek et al., 1989, *J. Gen. Microbiol.* 135:3303–3309). The correct reading frame was determined by computer analysis based on the high G+C content of the third position of codons (Wilson, 1992, *Crit. Rev. Biotech.* 12:45–63). A reading frame from nucleotides 475 to 2262 (as shown in SEQ ID NO:1) encodes a 596 amino acid protein that corresponds to the E3 precursor and has a G+C content of 91% in the third positions of the codons.

The E3 gene begins with ATG at nucleotide 475. However other possible translation start codons were present. ATGs are located at nucleotides 511 and 559 and GTG at 562. None of these have a ribosome-binding site or characteristic signal sequence while a potential ribosome-binding site is present 10 bases upstream of the initiational codon at 475. The sequence AAGGA, also found in the E1 gene, is perfectly complementary to the 3' end of both *S. lividans* 16S RNA and *E. coli* 16S RNA. The binding energy of this sequence to the 3' end of 16S RNA was calculated to be $\Delta G° = -10.6$ kcal/mol.

Primer extension analysis was performed to determine the transcriptional start site. Total RNA was purified from an *E. coli* strain containing pSZ4. An oligonucleotide (SEQ ID NO:3) complementary to a region coding for the signal peptide of E3 was synthesized and labelled at its 5' terminal with $^{32}$P r-ATP and polynucleotide kinase. Northern hybridization was then carried out to determine the size of E3 mRNA and was followed by primer extension experiments. Total RNA (50 µg) was hybridized to the $^{32}$P-labelled oligonucleotide. After addition of AMV reverse transcriptase, the labelled transcripts from the oligonucleotide extension, and regular DNA sequencing mixtures using the same oligonucleotide with pSZ4 plasmid DNA, were electrophoresed on a denaturing 6% polyacrymide sequencing gel that was autoradiographed. A single transcriptional start site was determined by primer extension to be at nucleotide 162, 313 bases upstream of the translational initiation codon. This long 5' untranslated sequence contains putative regulatory sequences and potential secondary structure. The size of E3 mRNA estimated by Northern hybridization is 2.0–2.1 kb which is in good agreement with the deduced size of the reading frame and the 5' untranslated region (2.1 kb), indicating monocistronic expression of the E3 gene.

A 14bp inverted repeat with the sequence 5' TGG-GAGCGCTCCCA 3' was located 211 bases before the translational start codon. This inverted sequence was previously identified by DNAse I footprinting as the binding site for a regulatory protein that is involved in induction by cellobiose (Lao et al., 1988, *J. Bacteriol.* 170:3843–3846). A gel retardation assay on the 5' flanking region of the E3 gene showed binding to the region containing the 14bp sequence by the protein present in *T. fusca* cell extracts. Directly preceding the 5' mRNA start site is a 13bp sequence that is identical to the 14bp binding site except for the 3' end A. This sequence also could be involved in the regulation of E3 expression on the basis of its similarity to the 14bp binding site and its location.

A sequence similar to a Rho-independent terminator in *E. coli* was found in the sequence downstream of the E3 structural gene. It contains a 14 base palindrome followed by four Ts and is able to form a stemloop structure with a $\Delta G°$ of −40.0 kcal/mol (ca. −167kj/mol) which agrees well with the free energy of known Streptomyces terminators. A similar potential mRNA stemloop structure also can be found in the E1 gene between nucleotides 3163–3202. Just following the putative terminator in the E3 gene is a second potential stemloop-forming sequence at nucleotides 2368–2409 which can also form a stable structure.

EMBODIMENT C

Expression of recombinant E3 and catalytically active polypeptide

This embodiment illustrates that a nucleic acid molecule comprising nucleotide sequences encoding E3 or portions thereof (ex. a polypeptide of E3 containing the catalytically active domain; herein referred to as catalytically active polypeptide), can be inserted into various vectors including phage vectors and plasmids. Successful expression of E3, and catalytically active polypeptides, requires that either the insert comprising the gene encoding E3, or the gene fragment encoding a catalytically active polypeptide, or the vector itself, contain the necessary elements for transcription and translation (expression control elements) which is compatible with, and recognized by the particular host system used for expression. DNA encoding E3 or catalytically active polypeptide, can be synthesized or isolated and sequenced using the methods and sequences as illustrated according to Embodiments A, and B herein. A variety of host systems may be utilized to express recombinant E3, and recombinant catalytically active polypeptide, which include, but are not limited to bacteria transformed with a bacteriophage vector, plasmid vector, or cosmid DNA; yeast containing yeast vectors; fungi containing fungal vectors; insect cell lines infected with virus (e.g. baculovirus); and mammalian cell lines transfected with plasmid or viral expression vectors, or infected with recombinant virus (e.g. vaccinia virus, adenovirus, adeno-associated virus, retrovirus, etc.).

Using methods known in the art of molecular biology, including methods described above, various promoters and enhancers can be incorporated into the vector or the nucleic acid molecule encoding E3 amino acid sequences, i.e. recombinant E3 or catalytically active polypeptide, to increase the expression of E3 amino acid sequences, provided that the increased expression of the E3 amino acid sequences is compatible with (for example, non-toxic to) the particular host cell system used. Thus and importantly, the nucleic acid molecule can consist of the gene encoding E3 protein, or any segment of the gene which encodes a functional/catalytically active domain of E3.

The selection of the promoter will depend on the expression system used. Promoters vary in strength, i.e. ability to facilitate transcription. Generally, for the purpose of expressing a cloned gene, it is desirable to use a strong promoter in order to obtain a high level of transcription of the gene and expression into gene product. For example, bacterial, phage, or plasmid promoters known in the art from which a high level of transcription has been observed in a host cell system comprising *E. coli* include the lac promoter, trp promoter, tac promoter, recA promoter, ribosomal RNA promoter, the $P_R$ and $P_L$ promoters, lacUV5, ompF, bla, lpp, and the like, may be used to provide transcription of the inserted DNA sequence encoding E3 amino acid sequences.

The use of a promoter to enhance the expression of E3 is illustrated in Embodiment A herein. It was noted that *E. coli* cells containing pSZ4 and pSZ6 in which the E3 gene is aligned with the lac promoter showed more CMCase activity and expressed more E3 by Western blot analysis than cells with pSZ3 or pSZ5 which have the gene in the opposite orientation. Similarly, the level of expression of E3 in *S. lividans* showed that expression was several fold greater when the gene (lacking the E3 promoter and probably most of the 5' regulatory sites) was orientated in the plasmid as in pSZ7, compared to the orientation in pSZ8. This suggests that the promoter is orientated in the same direction as E3 in pSZ6, and the tsr gene is the closest gene in pIJ702 with that orientation.

Other control elements for efficient gene transcription or message translation include enhancers, and regulatory signals. Enhancer sequences are DNA elements that appear to increase transcriptional efficiency in a manner relatively independent of their position and orientation with respect to a nearby gene. Thus, depending on the host cell expression vector system used, an enhancer may be placed either upstream or downstream from the inserted nucleic acid molecule encoding E3 amino acid sequences to increase transcriptional efficiency. As illustrated in Embodiment B, other specific regulatory sequences have been identified which may effect the expression from the gene encoding E3. These or other regulatory sites, such as transcription or translation initiation signals, can be used to regulate the expression of the gene encoding E3, or gene fragments encoding catalytically active polypeptide. Such regulatory elements may be inserted into nucleic acid molecules encoding E3 amino acid sequences or nearby vector DNA sequences using recombinant DNA methods described, for example in Embodiment A, for insertion of DNA sequences.

Accordingly, nucleic acid molecules containing regions encoding for E3, or catalytically active polypeptide can be ligated into an expression vector at a specific site in relation to the vector's promoter, control, and regulatory elements so that when the recombinant vector is introduced into the host cell, the E3-specific DNA sequences can be expressed in the host cell. For example, the E3-specific DNA sequences containing its own regulatory elements can be ligated into an expression vector in a relation or orientation to the vector promoter, and control elements which will allow for expression of E3 amino acid sequences. The recombinant vector is then introduced into the appropriate host cells, and the host cells are selected, and screened for those cells containing the recombinant vector. Selection and screening may be accomplished by methods known in the art including detecting the expression of a marker gene (e.g., drug resistance marker) present in the plasmid; immuno-screening for production of E3-specific epitopes using antisera generated to E3-specific epitopes; probing the DNA of the host cells for E3-specific nucleic acid molecules using one or more oligonucleotides and methods described according to Embodiment A herein; and an activity assay such as the CMC overlay assay.

Genetic engineering techniques may also be used to characterize, modify and/or adapt the recombinantly expressed E3 or catalytically active polypeptide. For example, site-directed mutagenesis to modify E3 cellulase in regions outside the catalytically active domain, may be desirable to increase the solubility of the cellulase or catalytically active polypeptide to allow for easier purification. Further, genetic engineering techniques can be used to generate nucleic acid molecules encoding E3 catalytically active polypeptide. For example, from the sequence disclosed as SEQ ID NO:1, it can be determined which restriction enzyme or combination of restriction enzymes may be used to generate nucleic acid molecules encoding catalytically active polypeptide. Restriction enzyme selection may be done so as not to destroy the catalytically active domain of the resultant polypeptide. Consequently, using SEQ ID NO:1 as a guide, restriction enzyme combinations may be used to generate nucleic acid molecules, which when inserted into the appropriate vector, are capable of directing the production of catalytically active polypeptide.

Plasmids constructed to express recombinant E3 in *E. coli* are illustrated according to Embodiment A. For expression of recombinant E3 in *Streptomyces lividans*, an *E. coli-S. lividans* shuttle plasmid, pSZ7, was constructed by inserting the insert from pSZ6 into pGG82 described in Ghangas et al. (1989, *J. Bacteriol.* 171:2963–2969). Both pSZ6 and pGG82 were digested with Hind III and Sph I. Two large fragments were isolated on a low melting agarose gel, ligated, and transformed into *E. coli* DH5α. The desired transformants were identified by restriction mapping of plasmid DNA and by the CMC overlay assay. To express E3 in *S. lividans*, pSZ7 was transformed into *S. lividans* strain TKM31 (a protease-negative strain isolated from *S. lividans* TK24) protoplasts on R2YE plates. After incubation for 16 hours at 30° C., transformants were selected by overlaying the plates with nutrient agar containing thiostrepton (50 µg/ml) in plates. Transformants were then screened by the CMC overlay assay and by restriction digestion of plasmid DNA which was prepared from 20 ml tryptone soya broth cultures of the desired *S. lividans* transformants.

EMBODIMENT D

Production of catalytically active polypeptide by cleavage of E3

To determine the catalytically active domain of E3, E3 may be cleaved into peptides using methods of chemical or enzymatic cleavage with agents known to those in the art. One method that may be used is to cleave E3 using cyanogen bromide as described according to Embodiment A. The resultant cyanogen bromide cleaved peptides of TE3 were measured by mass spectrometry. TE3 cleaved by CNBr released six peptides with molecular masses of 21,745, 7,310, 4,374, 13,800, 9,957 and 4,748 Da that correlate well with the values of 20,084, 6,671, 4,288, 14,100, 9,865 and 4,728 predicted from the positions of the methionine residues in the sequence. The only significant differences between the predicted and measured values are in the first two peptides which are 10% higher then predicted. The first peptide, 21,745 Da contains the cellulose binding domain and the linker peptide and these results show that most of the sugar in E3 appears to be in those regions.

A method to generate a catalytically active polypeptide, and to detect variations in the proteolytic resistance of TE3, SrE3, and ErE3, is by degradation by papain. Unlike other *T. fusca* cellulases (E2 and E5), recombinant E3 appears to be stable in vivo. Even after 3–5 days of growth in TES-Hag medium, secreted SrE3 remained intact. Thus, partial digestion of E3 by papain was used to produce an E3 catalytically active peptide. A purified preparation of each of TE3, SrE3, and ErE3 was partially digested with papain as follows: 15 µl of 1.0 mg/ml papain solution in 0.05M NH$_4$Ac buffer, 5 mM L-cysteine and 2 mM EDTA pH6.5 were added to 100 µg of purified E3 from each source in 85 µl of 0.05M NH$_4$Ac pH6.5. The mixtures were incubated at 37° C. and aliquots (2–10 µl) were removed at 0.5 hours, 1 hour, 2 hours, 4 hours, 8 hours and 24 hours for further analysis by both SDS-PAGE and native PAGE followed by a CMC overlay (Beguin, 1983, *Anal. Biochem.* 131:333–336). Intact E3 was completely converted to a 46kDa fragment containing the catalytic domain (catalytically active polypeptide E3cd; SEQ ID NO:4) by a 60 minute digestion with papain under the given conditions. No further degradation appeared even after 24 hours of digestion. The only bands visualized by Coomassie blue staining were intact E3 and E3cd from each source. It is likely that the binding domain and linker region have been completely degraded. The molecular mass of E3cd on SDS-PAGE was not influenced by reduction, suggesting that no additional cleavage site existed in E3cd. A CMC overlay of a native gel showed that E3cd possessed similar CMCase activity to E3.

The exact molecular weight of E3cd produced from each form of E3 was determined by mass spectrometry. All three forms gave a value of 46kDa(TE3cd:46,092 Da; SrE3cd: 46013 Da; and ErE3cd: 46,067 Da) which is very close to the predicted molecular mass of 45,707 Da. The fact that all three forms of E3cd have the same molecular mass indicates that all of the sugar in TE3 is present in the binding domain and linker region. This conclusion is also supported by the results of the determination of the molecular weight of the peptides generated by cyanogen bromide cleavage and by glycosylation assays of E3cd.

EMBODIMENT E

Purification of recombinant E3 or catalytically active polypeptide

Recombinant E3 or a catalytically active polypeptide can be purified, to then be used for the particular industrial application desired, using methods known in the art for purifying recombinant proteins from host cell systems including detergent extraction, chromatography (e.g. ion exchange, affinity, immunoaffinity, sizing columns, or a combination thereof), differential centrifugation, differential solubility, or other standard techniques for the purification of proteins. One illustrative example of how recombinant E3 or a catalytically active polypeptide can be purified is to use the method disclosed in Embodiment A for the purification of *T. fusca* E3 from culture supernatant.

For purification of recombinant E3 from *E. coli*, an overnight superbroth culture (10 ml) of *E. coli* transformed with pSZ6 was inoculated into 1 liter of same medium (Luria broth with ampicillin at 100 μg/ml). The culture was grown for 22 hours with rotary shaking at 37° C., and centrifuged at 5000 rpm for 15 minutes. The pellet was resuspended in 50 ml of 0.05M NaCl pH5.5+1 mM phenylmethylsulfonyl fluoride (PMSF); French pressed at 10,000 lb/in$^2$; and centrifuged at 10,000 rpm for 30 minutes. The lysate was adjusted to 0.25M $(NH_4)_2SO_4$+1 mM glucanolactone and loaded onto a cellobioside affinity column (2.5×10 cm) that was previously equilibrated with the same buffer. The column was washed with 2 volumes of equilibration buffer, 2 volumes of 0.05M NaCl pH5.5+1 mM glucanolactone, and then 0.02M cellobiose in wash buffer was used to elute E3. Further purification was performed on the anion exchange column as described above in Embodiment A for purification of E3 from *T. fusca*. Using this technique, recombinant E3, produced from *E. coli*, was shown to be 95% pure by SDS PAGE. Catalytically active polypeptide, produced from *E. coli* transformed with a vector engineered to produce catalytically active polypeptide, may be purified from the transformed *E. coli* using the same or a similar method.

Recombinant E3 produced in *S. lividans* was purified from a 10-liter culture of *S. lividans* transformed with pZS7. A 3-day culture of *S. lividans* pSZ7 (25 ml) in tryptone soya broth was used to inoculate 250 ml of same medium. After growth for 48 hours at 30° C. the entire culture was added to 10-liters of the same medium. Mycelia were harvested after 72 hours of fermentation (agitation, 200 rpm; air flow, 1 volume of air per volume of medium per minute; temperature, 30° C.; pH, initially at 7.1) by cross-flow filtration with a Millipore Pelicon cassette equipped with 0.45 μm membranes. All purification procedures were carried out at 4° C. PMSF and ammonium sulfate were added to mycelia-free supernatant at 0.1 mM and 1M final concentrations respectively. The supernatant was loaded onto a phenyl-SEPHAROSE™ column (10×14 cm) which was equilibrated with 0.6M $(NH_4)_2SO_4$, 0.01M NaCl, 0.005M Kpi pH6.0. The column was washed with 2 volumes of equilibration buffer, followed by 2 volumes of 0.3M $(NH_4)_2SO_4$, 0.01M NaCl, 0.005M Kpi pH6.0, and then the protein was eluted with 0.005M Kpi pH6. The fractions containing activity were combined and adjusted to 0.25M $(NH_4)_2SO_4$, 1 mM glucanolactone by adding solid $(NH_4)_2SO_4$ and glucanolactone and applied to a p-nitrobenzyl 1-thio-β-D-cellobioside affinity column that was equilibrated with 0.25M $(NH_4)_2SO_4$, 1 mM glucanolactone, 0.005M Kpi pH6.0. After loading, the column was washed with 2 volumes of 0.1M $(NH_4)_2SO_4$, 1 mM glucanolactone, 0.005M Kpi pH6.0 and then 2 volumes of 0.1M NaAc buffer pH5.5+1 mM glucanolactone. Recombinant E3 was eluted by the addition of 0.1M lactose to the wash buffer. The appropriate fractions were finally applied to a anion exchange column equilibrated with 0.1M NaAc buffer pH5.5. After washing with 0.2M NaCl, 0.02M Bistris pH5.1, a linear gradient from 0.2–0.5M NaCl was used to elute recombinant E3. Using this technique, recombinant E3, produced from *S. lividans* was shown to be 95% pure by SDS PAGE. Catalytically active polypeptide, produced from *S. lividans* transformed with a vector engineered to produce catalytically active polypeptide, may be purified from the transformed *S. lividans* using the same or similar method.

To isolate E3cd, 15 mg of each of the three sources of E3 was partially digested by papain for 1 hour and chromatographed by gel filtration on a ACA54 column(2.6×100 cm) with 0.05M NaAc buffer pH5.5. The eluates were analyzed by SDS-PAGE which showed confirmed that E3cd was purified to 99% homogenity.

EMBODIMENT F

Physicochemical characterization of recombinant E3 and catalytically active polypeptide 1. Protein size and amino acid composition The protein size and compositions of the recombinant E3 produced in *E. coli* ("ErE3") and produced in *S. lividans* ("SrE3") were compared with E3 isolated from *T. fusca* ("TE3"). The molecular mass of TE3 was estimated from SDS-PAGE as being about 65,000 daltons (Da). All three forms of E3 display nearly identical electrophoretic mobilities on a 12% SDS gel. On an 8.5% native polyacrylamide gel ErE3 was found to move a little faster than TE3 and SrE3 (FIG. 1A). The N-terminal sequences of the ErE3 (SEQ ID NO:5), SrE3 (SEQ ID NO:6; SEQ ID NO:7) and TE3 (SEQ ID NO:8) show that all three organisms use the same site for signal peptide cleavage but, in *S. lividans* there is an additional cleavage site at six amino acids before the regular site. It appears that *S. lividans* prefers to use the alternate site removing a 32 amino acid instead of a 38 amino acid signal sequence since 70% of SrE3 has AlaAlaProAlaGlnAla as its N-terminus and 30% has AlaGlyCysSerValAsp.

The amino acid compositions deduced from the open reading frame agree well with the experimentally determined values for the native protein (TE3), recombinant proteins (SrE3, ErE3) and E3cd (Table 1). Furthermore, the predicted molecular mass of the mature protein is 59,646 Da which is a little smaller than that estimated from SDS PAGE. The deduced molecular mass is consistent with that of ErE3 (59,797 Da) as determined by mass spectrometry while that of TE3 (61,200 Da) is larger as expected for a glycoprotein and that for Sr E3 (61,169 Da) is about 900 Da larger than the value calculated from its N terminus which is consistent with it also being a glycoprotein.

TABLE 1

Comparison (mol %) of predicted and experimentally determined amino acid compositions of three forms of E3 and E3cd

| Amino acid | Predicted | ErE3 | SrE3 | TE3 | Predicted | 7E3cd |
|---|---|---|---|---|---|---|
| Ala | 7.9 | 8.2 | 8.5 | 8.1 | 9.0 | 9.4 |
| Arg | 3.4 | 3.3 | 3.5 | 3.2 | 4.5 | 5.3 |
| Asx | 15.8 | 16.1 | 16.1 | 16.5 | 15.6 | 13.9 |
| Cys | 1.1 | 0.2 | 0.4 | 0.5 | 1.0 | 0.2 |
| Gly | 11.5 | 14.3 | 13.4 | 13.3 | 11.3 | 13.0 |
| Glx | 7.7 | 8.1 | 7.9 | 9.1 | 8.3 | 8.3 |
| His | 1.2 | 1.0 | 1.0 | 1.1 | 1.4 | 1.2 |
| Ile | 5.0 | 4.5 | 4.6 | 4.6 | 5.7 | 5.4 |
| Leu | 5.6 | 5.6 | 5.7 | 5.5 | 6.4 | 6.9 |
| Lys | 2.0 | 1.7 | 1.7 | 2.1 | 2.4 | 2.1 |
| Met | 0.9 | 0.8 | 0.8 | 0.1 | 1.2 | 0.8 |
| Pro | 8.2 | 8.8 | 8.9 | 7.3 | 6.9 | 8.2 |
| Phe | 2.7 | 2.6 | 2.7 | 2.6 | 2.4 | 2.5 |
| Ser | 8.2 | 9.1 | 9.0 | 9.5 | 6.6 | 6.1 |
| Thr | 5.4 | 5.5 | 5.7 | 6.3 | 3.8 | 4.3 |
| Tyr | 4.1 | 4.2 | 4.3 | 4.3 | 4.5 | 5.9 |
| Val | 6.5 | 5.8 | 5.9 | 6.0 | 6.6 | 6.4 |
| Trp | 2.7 | f | f | f | 2.6 | f |
| f– | | | | | | |

2. Glycosylation of E3, recombinant E3, and E3cd

Figure 1B:
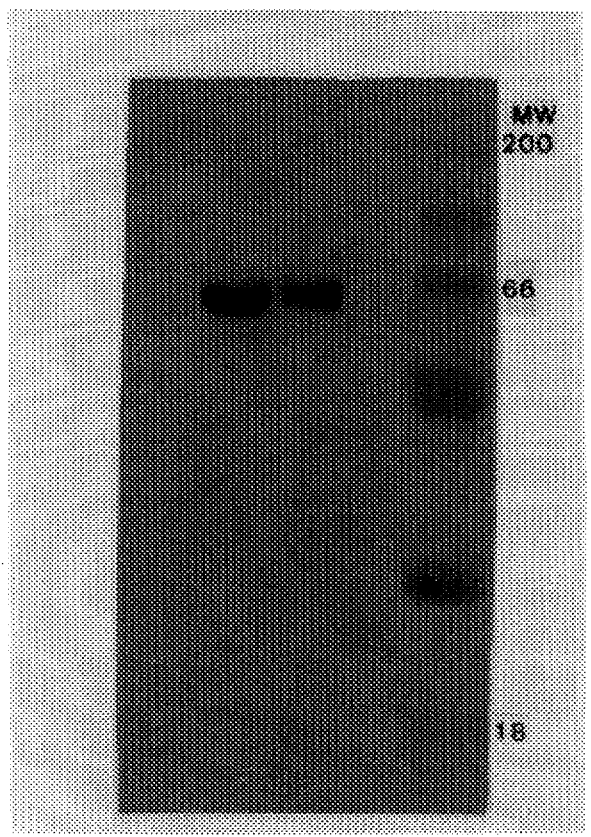

In a previous study, *T. fusca* E3 was shown to be glycosylated having a sugar content estimated at 5% (Wilson, 1988, Methods Enzymol. 160:314–323). To determine if glycosylation of the recombinant E3 and E3cd varied from that of TE3, the respective purified proteins were analyzed for glycosylation by a glycan detection kit using the following method. Protein (2–10 µg) was dissolved in 10 µl of 0.1M NaAc buffer pH5.5 and oxidized by the addition of 10 µl 10.015M sodium metaperiodate at 25° C. for 20 minutes in the dark. After destroying the excess periodate, the protein was labeled with digoxigenin 3-0-succinyl-ε-aminocaprioc acid hydrazide hydrochloride, electroblotted onto nitrocellulose membranes and detected with anti-digoxigenin antibody coupled to alkaline phosphatase. The results show that ErE3 lacked measurable sugar (FIG. 1B) but displayed nearly identical enzymatic properties and electrophoretic mobilities (FIG. 1A) on an SDS-gel to TE3, while SrE3 was partially glycosylated. However no sugar was detected in TE3cd, also suggesting that all carbohydrate occurs in the binding domain and linker region of E3. Recently it was reported that no glycosylation of an endocelluase lacking a binding domain cloned in *S. lividans* could be detected by this assay (Fernando-Abalos et al., 1992, *J. Bacteriol.* 174:6368–6376), and its own cellulase was glycosylated (Theberge et al., 1992, *Appl. Environ. Microbiol.* 58: 815–820). The fact that no difference was observed in enzymatic activity, cellulose binding, or stability to proteolysis between TE3, ERE3, and SrE3 indicates that glycosylation appears not to be required for these functions.

3. Enzymatic activity, and binding properties of recombinant E3 and E3cd.

To determine the specific activities and binding properties of the different recombinant E3 and E3cd, carboxymethylocellulose (CMC) and filter paper were used as substrates. Native cellulose is both insoluble and structurally heterogeneous, thereby making it difficult for comparing activities between different enzymes or enzyme combinations. Thus, the amount of enzyme to achieve digestion of 5.2% of the substrate (ex. filter paper) in 16 hours was determined, as recommended in the International Union of Pure and Applied Chemistry Commission on Biotechnology report, "Measurements of Cellulase Activities" (Ghose, 1987, *Pure Appl. Chem.* 59:257–268).

CMCase assays were carried out by adding to 1% CMC (low viscosity, degree of substitution average =0.7 of 3 possible hydroxyls per monomeric unit) the cellulase, or catalytically active polypeptide, to be tested in 0.05M Na acetate bufer, pH 5.5. The cellulase or catalytically active polypeptide was added to give a total volume of 400 µl and the samples were incubated for 16 hours at 50° C. To measure the amount of reducing sugar produced, 1 ml of dinitrosalicylic acid reagent (DNS) was added and the samples were placed in a boiling water bath for 15 minutes. After cooling the samples to room temperature, the optical densities were measured at 600 nm. All proteins were quantitated by their A280 nm using predicted extinction coefficients. Filter paper assays were carried out as above for the CMCase assays except that single discs of filter paper (3.4 mg) were used as the substrate. The results of these assays, comparing the activities of the TE3 with recombinant E3s and with E3cd, are shown in Table 2.

TABLE 2

Activity assays of TE3 and cloned products (ErE3 and SrE3) and E3cd

| | Activity (µmol. CB/min, µmol enzyme)[b] | |
|---|---|---|
| Enzyme | CMC | Filter paper |
| TE3 | 0.62 | 0.153 |
| SrE3 | 6.53[c] | 0.373[c] |
| ErE3 | 0.65 | 0.157 |
| E3cd | 0.48 | 0.050 |

[b]Extinction coefficients for E3(115150/molar) and E3cd(87150/molar) were determined from the predicted sequence.
[c]Contaminating CMC activity as detemined by a CMC overlay of native gel.

Figure 2:
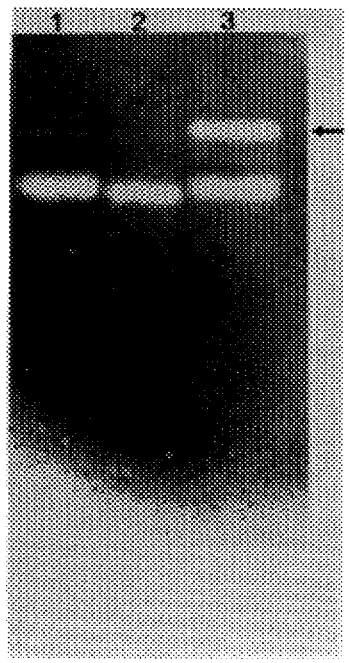
FIG. 2 represents the electrophoretic mobility of 10 μg of each of TE3 (lane 1), ErE3 (lane 2), and SrE3 (lane 3), on a 8.5% polyacrylamide gel stained with Congo red to detect CMCase activity.

The results, shown in Table 2, indicate that ErE3 had nearly identical enzymatic activity to TE3 in hydrolyzing either filter paper or CMC. However, SrE3 had ten times the activity of TE3 and ErE3 on CMC, and twice as much activity as TE3 and ErE3 on filter paper. A CMC overlay of a native gel on SrE3 clearly showed that SrE3 contained a CMCase from *S. lividans* (FIG. 2, lane 3, band above SE3). Thus, the increased enzymatic activity of SrE3, over that of TE3 and ERE3, may be due to the contaminating CMCase. E3cd retained 77% of the activity of TE3 on CMC but only 33% of the activity of TrE3 on filter paper.

The ability of each of TE3, ERE3, SrE3 and E3cd to bind to cellulose was determined by adding 266 µg of the enzyme to 0, 5 mg, 10 mg, 25 mg, 50 mg, and 100 mg of Avicel in 1 ml of 0.05M sodium acetate buffer pH 5.5. The samples were incubated at 50° C. for 1 hour with end over end rotation. After centrifugation, the amount of the enzyme left in the supernatant was measured by A280 nm. The results of the binding assay indicate that the binding of TE3, ERE3, and SrE3 were very similar. However, E3cd bound much more weakly than TE3 (approx. 1% vs. 100% for TE3).

EMBODIMENT G

Unexpected hydrolytic activity of the combination of E3, E5, and CBHI

In this embodiment is illustrated that recombinant E3 can be included in a combination of cellulases that together exhibit unexpected hydrolytic activity at a high temperature range (preferably between 50° C.–60° C.); i.e. the hydrolytic activity of the combination of cellulases is greater than the sum of the hydrolytic activities of the individual cellulases found in the combination. Disclosed is a combination of at least three types of cellulases which effectively hydrolyzes microcrystalline cellulose. The three types of cellulases include an effective endocellulase such as T. fusca E2 or E5; exocellulase rE3; and a cellobiohydrolase such as Trichoderma reesei CBHI. In considering the potential for achieving higher rates and extents of hydrolysis with the cellulase combination, the role of product inhibition was considered in determining the proper mole fraction of cellulases comprising the combination (Walker et al., 1993, Biotechnol. Bioeng. 42:1019–1028, the disclosure of which is incorporated herein by reference). E2 and E5, recombinantly produced in S. lividans, as well as E5cd can be purified by methods described previously (Irwin et al., 1993, Biotechnol. Bioeng. 42:1002–1013, the disclosure of which is incorporated herein by reference). T. reesei CBHI can be purified by the methods described previously (Irwin et al., 1993, supra). To determine the specific activities of the different cellulase combinations, filter paper was used as a substrate according to the methods of Embodiment F. The enzymatic activities of different cellulase combinations are shown in Table 3. Further hydrolysis can be accomplished by the addition of a β-glucosidase to the combination.

TABLE 3

Activity assay of cellulase combinations

| Enzyme[a] | Activity (μmol CB/min, μmol enzyme)[b] Filter paper |
|---|---|
| TE3 + E5 | 2.61 |
| SrE3 + E5 | 2.89 |
| ErE3 + E5 | 2.85 |
| E3cd | 1.18 |
| TE3 + E5cd | 2.15 |
| E3cd + E5cd | 1.21 |
| TE3 + E5 + CBHI | 7.46 |
| SrE3 + E5 + CBHI | 6.52 |
| ErE3 + E5 + CBHI | 7.56 |
| E3cd + E5 + CBHI | 3.37 |
| TE3 + E5cd + CBHI | 6.53 |
| E3cd + E5cd + CBHI | 3.87 |

[a] molar ratios of the mixture components were 4:1 for E3:E5, and 2:1:2 for E3:E5:CBHI
[b] Extinction coefficients for E3 (115150/molar) and E3cd (87150/molar) were determined from the predicted sequence.

The results in Table 3 show that when recombinant E3 was used in the combination according to the present invention, the unexpected hydrolytic activity was similar to that seen when TE3 was used in the combination. In the reactions involving combinations and their hydrolysis of filter paper, it appears that the contaminating enzyme of S. lividans (CMCase) did not affect activity of combinations containing SrE3.

In using the combination of the present invention (recombinant E3, an endocellulase such as E5, and a cellobiohydrolase such as T. reesei CBHI), the total concentration of cellulases in the combination may be from about 5 μM to about 15 μM with a preferred concentration range of from about 8 μM to about 12 μM. Of the total cellulase concentration, the preferred individual cellulase concentrations are rE3-20%–40%; endocellulose-15%–20%; and cellobiohydrolase-40%–65%. The pH range of the reaction will depend on the pH range of activity for the three cellulases comprising the combination. For example, if the cellobiohydrolase used in the combination is CBHI, the pH range in which the combination of cellulases may be used is about pH 3–5. CBHI is only active in that narrow pH range.

In another mode of this embodiment, and using the same total concentration of cellulases in the combination and the preferred individual concentrations of cellulases of the total cellulase concentration, β-glucosidase may be added to the combination (preferably from about 4IU to about 14IU per 12 μM total concentration of the combination of cellulases) to increase hydrolysis of the substrate such as cellulose or cellobiose.

It should be understood that while the invention has been described in detail herein, the examples were for illustrative purposes only. Other modifications of the embodiments of the present invention that are obvious to those skilled in the art of molecular biology, enzymology, industrial biotechnology, and related disciplines are intended to be within the scope of the appended claims.

What is claimed is:

1. An isolated and purified nucleic acid molecule which comprises a DNA sequence selected from the group consisting of SEQ ID NO:1, and SEQ ID NO:4, wherein SEQ ID NO:4 encodes a catalytically active polypeptide.

2. A vector comprising the nucleic acid molecule of claim 1.

3. A host cell containing the vector of claim 2, wherein said host cell is not *Thermomonospora fusca*.

4. The host cell of claim 3 wherein the host cell is selected from the group consisting of *E. coli* and *S. lividans*.

5. A recombinant cellulase isolated and purified from the host cell of claim 2.

6. A recombinant cellulase isolated and purified from the host cell of claim 4.

7. An isolated and purified nucleic acid molecule encoding a protein or polypeptide having cellulase activity, wherein the protein or polypeptide is selected form the group consisting of:

a. E3, consisting of the amino acid sequence encoded by SEQ ID NO:1; and b. E3cd, consisting of the amino acid sequence encoded by SEQ ID NO:4, wherein E3cd is a catalytically active polypeptide of E3.

8. A recombinant vector containing the nucleic acid molecule according to claim 7, wherein the nucleic acid molecule is operatively linked to one or more control elements for expression.

9. A host cell containing the vector of claim 8.

10. The host cell of claim 9 wherein the host cell is selected from the group consisting of *E. coli* and *S. lividans*.

11. A method of hydrolyzing a substrate selected from the group consisting of cellulose, and chitosan comprising contacting the substrate with the recombinant cellulase according to claim 5 in a reaction having a pH in a range of 5–11, and a temperature in a range of 40°–70° C.

12. A method of hydrolyzing a substrate selected from the group consisting of cellulose, and chitosan comprising contacting the substrate with the recombinant cellulase according to claim 6 in a reaction having a pH in a range of 5–11, and a temperature in a range of 40°–70° C.

13. A combination of cellulases that hydrolyzes cellulose with unexpected hydrolytic activity said combination of cellulases comprising a first cellulase consisting of the recombinant cellulase according to claim 5, a second cellulase consisting of an endocellulase, and a third cellulase consisting of cellobiohydrolase CBHI, wherein the percentage of the total cellulase comprising the combination for each cellulase in the combination to achieve optimal unexpected hydrolytic activity is from about 20% to about 40% for the first cellulase, from about 15% to about 20% for the second cellulase, and from about 40% to about 65% for the cellobiohydrolase, and further comprising β-glucosidase.

14. A combination of cellulases that hydrolyzes cellulose with unexpected hydrolytic activity said combination of cellulases comprising a first cellulase consisting of the recombinant cellulase according to claim 6, a second cellulase consisting of an endocellulase, and a third cellulase consisting of cellobiohydrolase CBHI, wherein the percentage of the total cellulase comprising the combination for each cellulase in the combination to achieve optimal unexpected hydrolytic activity is from about 20% to about 40% for the first cellulase, from about 15% to about 20% for the second cellulase, and from about 40% to about 65% for the cellobiohydrolase, and further comprising β-glucosidase.

15. The combination according to claim 13, wherein the second cellulase is E5.

16. The combination according to claim 14, wherein the second cellulase is E5.

* * * * *